United States Patent
Valencia et al.

(10) Patent No.: US 10,725,019 B2
(45) Date of Patent: Jul. 28, 2020

(54) MICROFLUIDIC CHIP FOR COAGULATION SENSING

(71) Applicant: Hewlett-Packard Development Company, L.P., Houston, TX (US)

(72) Inventors: Melinda M Valencia, San Diego, CA (US); Chantelle E Domingue, Corvallis, OR (US); Jeremy Sells, Corvallis, OR (US); Manish Giri, Corvallis, OR (US); Sadiq Bengali, Corvallis, OR (US)

(73) Assignee: Hewlett-Packard Development Company, L.P., Spring, TX (US)

( * ) Notice: Subject to any disclaimer, the term of this patent is extended or adjusted under 35 U.S.C. 154(b) by 249 days.

(21) Appl. No.: 15/522,831

(22) PCT Filed: Jan. 30, 2015

(86) PCT No.: PCT/US2015/013668
§ 371 (c)(1),
(2) Date: Apr. 28, 2017

(87) PCT Pub. No.: WO2016/122559
PCT Pub. Date: Aug. 4, 2016

(65) Prior Publication Data
US 2017/0328882 A1    Nov. 16, 2017

(51) Int. Cl.
*G01N 27/02* (2006.01)
*B01L 3/00* (2006.01)
(Continued)

(52) U.S. Cl.
CPC ........ *G01N 33/4905* (2013.01); *B01L 3/5027* (2013.01); *B01L 3/502715* (2013.01);
(Continued)

(58) Field of Classification Search
CPC ........ G01N 15/06; G01N 33/00; G01N 33/48; G01N 35/00; G01N 1/10; G01N 1/2702;
(Continued)

(56) References Cited

U.S. PATENT DOCUMENTS

| | | |
|---|---|---|
| 6,046,051 A | 4/2000 | Jina |
| 7,005,857 B2 | 2/2006 | Stiene et al. |

(Continued)

FOREIGN PATENT DOCUMENTS

| | | |
|---|---|---|
| CN | 101858878 | 1/2009 |
| JP | H08-501153 | 2/1996 |

(Continued)

OTHER PUBLICATIONS

Berney, et al.; Impedance Measurement Monitors Blood Coagulation; Aug. 2008; http://www.analog.com/library/analogdialogue/archives/42 08/blood_coagulation.pdf.

(Continued)

*Primary Examiner* — Brian J. Sines
(74) *Attorney, Agent, or Firm* — Fabian VanCott

(57) ABSTRACT

Example implementations relate to coagulation sensing. For example, a microfluidic chip for coagulation sensing may include a microfluidic channel, an outlet at an end of the microfluidic channel having an air interface, and an impedance sensor located within the microfluidic channel and within a particular proximity to the air interface, the impedance sensor to determine a stage of a coagulation cascade of a blood sample flowing through the microfluidic channel to the impedance sensor.

17 Claims, 4 Drawing Sheets

(51) Int. Cl.
*G01N 33/49* (2006.01)
*B81B 1/00* (2006.01)

(52) U.S. Cl.
CPC ............. *B81B 1/00* (2013.01); *B01L 3/50273* (2013.01); *B01L 2300/0636* (2013.01); *B01L 2300/0645* (2013.01); *B01L 2300/0681* (2013.01); *B01L 2300/0864* (2013.01); *B01L 2300/1827* (2013.01); *B01L 2400/0442* (2013.01); *G01N 27/02* (2013.01)

(58) Field of Classification Search
CPC ....... G01N 27/021; B01L 3/00; B01L 3/5027; B01L 3/502715
USPC ........... 422/68.1, 502, 503, 504; 436/43, 63, 436/178, 180
See application file for complete search history.

(56) References Cited

U.S. PATENT DOCUMENTS

| | | | |
|---|---|---|---|
| 2004/0072357 A1 | 4/2004 | Stiene | |
| 2004/0147032 A1 | 7/2004 | Martin et al. | |
| 2005/0118705 A1* | 6/2005 | Rabbitt | B01L 3/502761 435/287.1 |
| 2006/0034809 A1* | 2/2006 | Ho | A01N 1/00 424/93.7 |
| 2006/0189863 A1* | 8/2006 | Peyser | A61B 5/0031 600/345 |
| 2008/0124749 A1 | 5/2008 | Farnam et al. | |
| 2008/0294029 A1 | 11/2008 | Piveteau et al. | |
| 2009/0051716 A1 | 2/2009 | Beebe et al. | |
| 2010/0094110 A1* | 4/2010 | Heller | A61B 5/14532 600/345 |
| 2011/0109325 A1 | 5/2011 | Huang et al. | |
| 2011/0244595 A1 | 10/2011 | Chung et al. | |
| 2012/0039770 A1* | 2/2012 | Namkoong | B01L 3/502738 422/504 |
| 2012/0142032 A1 | 6/2012 | Morgan et al. | |
| 2014/0014509 A1 | 1/2014 | Yan et al. | |
| 2014/0038299 A1 | 2/2014 | Sadaba Champetier De Ribes et al. | |
| 2014/0051161 A1 | 2/2014 | Bergstedt et al. | |
| 2014/0073027 A1 | 3/2014 | Dholakia et al. | |
| 2014/0161668 A1* | 6/2014 | Colella | B01L 3/502715 422/73 |
| 2014/0220617 A1 | 8/2014 | Yung et al. | |

FOREIGN PATENT DOCUMENTS

| | | |
|---|---|---|
| JP | H09-504372 | 4/1997 |
| JP | 2009-517654 | 4/2009 |
| TW | 201135226 | 10/2011 |
| WO | WO-2013040562 A2 | 3/2013 |
| WO | WO-2014/046687 | 3/2014 |
| WO | WO-2014104761 | 7/2014 |
| WO | WO-2014162285 | 10/2014 |
| WO | WO-2014178827 | 11/2014 |
| WO | WO-2015116083 | 8/2015 |

OTHER PUBLICATIONS

Guhr et al.; Novel Sensor Combining Impedance Spectroscopy and Surface Acoustic Waves to Detect Blood Coagulation Time and Hematocrit Value; Oct. 28-31, 2011; Http://ieeexplore ieee org/stamp/stamp jsp?arnumber=6127110.

Dou et al; "Microfluidic Impedance Sensor for Tumor Associated Procoagulant Activity"; Oct. 26-30, 2014—18th International Conference on Miniaturized Systems for Chemistry and Life Sciences; pp. 9266-9928.

* cited by examiner

MICROFLUIDIC CHIP FOR COAGULATION SENSING

BACKGROUND

Microfluidics is a technology that applies across a variety of disciplines including engineering, physics, chemistry, microtechnology and biotechnology. Microfluidics involves the study of small volumes of fluid and how to manipulate, control and use such small volumes of fluid in various microfluidic systems and devices such as microfluidic chips. For example, microfluidic biochips (referred to as "lab-on-chip") are used in the field of molecular biology to integrate assay operations for purposes such as analyzing enzymes and DNA, detecting biochemical toxins and pathogens, diagnosing diseases, etc.

DETAILED DESCRIPTION

Microfluidic chips may be employed in point of care testing to enable assay operations at a location associated with an individual to be tested. For example, in various point of care approaches to microfluidic testing a sample may be analyzed by a sensor in microfluidic testing device to give an indication of a disease state, among other possible conditions.

A living cell is the basic structural and functional unit of an organism. Most animal and plant cells range in size from 1-100 micrometers and contain vital health information. Cell-based diagnostics may be used for detecting infectious diseases, chronic diseases, and various biological abnormalities such as blood clotting disorders. Traditional cellular level diagnostic tools may, for example, be expensive, involve specialized training to operate, and may not always be deployed at the point-of-care setting. Furthermore, healthcare is gradually migrating away from centralized hospitals to a more distributed and/or in-home settings. This transition may, for example, involve the use of technology that provides the same level of performance and functionality as tests that are done in hospitals using sophisticated machinery, although in a smaller and more portable form.

Some diagnostic tools are capable of measuring coagulation rates of blood samples. However, such diagnostic tools require the use of reagents and/or activating agents to accelerate coagulation rates to a measurable level. Similarly, such diagnostic tools do not determine a particular stage of the coagulation cascade at which a blood sample might be in. In contrast, a microfluidic chip in accordance with the present disclosure may include an impedance sensor to determine a stage of a coagulation cascade, without the addition of reagents and/or activating agents to accelerate the coagulation process.

For purposes of this disclosure, the term "microfluidic" refers to devices and/or passages which interact with fluids having a volume or carrying particles having dimensions in the "micro" range, microliter or micrometer, respectively. For purposes of this disclosure, the term "particle" encompasses any small minute piece, fragment or amount, including, not limited to, a biological cell or group of biological cells. A "fluid" may comprise a liquid, a gas or mixtures thereof. Additionally, a "biologic sample" refers to blood and/or blood components such as blood plasma and/or blood serum, among other components.

Figure 1:
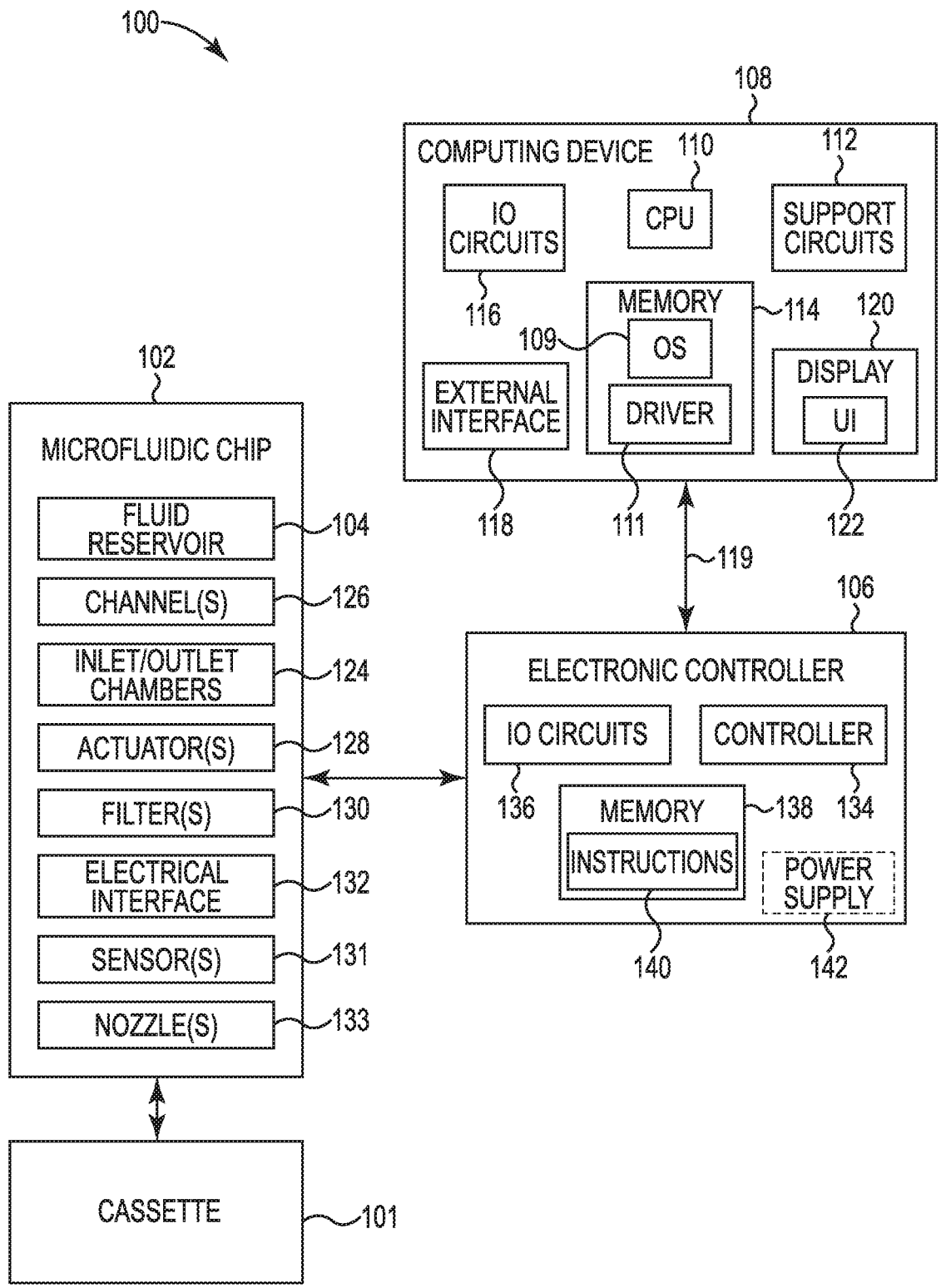
FIG. 1 illustrates an example of a microfluidic sensing system according to the present disclosure.

FIG. 1 illustrates an example of a microfluidics sensing system 100, according to the present disclosure. As illustrated in FIG. 1, the microfluidic sensing system 100 includes a microfluidic chip 102, a fluid reservoir 104, an electronic controller 106, and a computing device 108. In general, a sample of fluid may be placed in the fluid reservoir 104. In some examples, the fluid may have a volume as low as 10 pico-liters (pL) and as high as 1 micro-liter (µL). The fluid may be a host fluid having particles (e.g., a blood sample, an ink containing pigments/particles, or the like). As discussed further herein, the fluid may be processed through microfluidics on the microfluidic chip 102 and applied to a sensor in the microfluidic chip 102 under control of the electronic controller 106 and the computing device 108. The microfluidic chip 102 may provide an electrical output signal representing sensed data to the electronic controller 106.

The electronic controller 106 may be under control of the computing device 108. For example, the computing device 108 may send and receive data to and from the electronic controller 106, including command information for controlling the microfluidic chip 102 and sensor data obtained from the microfluidic chip 102.

The computing device 108 may include a central processing unit (CPU) 110, various support circuits 112, memory 114, various input/output (I/O) circuits 116, and an external interface 118. In some examples, a microfluidics application may be installed on the computing device 108. As used herein, a microfluidics application refers to instructions executed by a processing resource that direct the processing resource to perform a microfluidics sensing test. For example, the microfluidics application may include instructions executed by the electronic controller 106 and microfluidic chip 102 to perform coagulation sensing, as described further herein.

The support circuits 112 may include cache, power supplies, clock circuits, data registers, and the like. The memory 114 may include random access memory, read only memory, cache memory, magnetic read/write memory, and/or any combination of such memory devices. The I/O circuits 116 may cooperate with the external interface 118 to facilitate communication with the electronic controller 106 over a communication medium 119. The communication medium 119 may be any type of transfer path, including an electrical, optical, and/or radio frequency (RF) path.

The external interface 118 may include a universal serial bus (USB) controller capable of sending and receiving data to the electronic controller 106, as well as providing power to the electronic controller 106, over a USB cable. Further, the electronic controller 106 may receive a cassette 101 coupled to the microfluidic chip 102. For example, the microfluidic chip 102 may be mechanically inserted into the cassette 101, and the cassette 101 (having the microfluidic chip 102 coupled thereto) may be inserted into the electronic controller 106.

The memory 114 may store an operating system (OS) 109 and a driver 111. The OS 109 and the driver 111 may include instructions executable by the CPU 110 for controlling the computing device 108 and the electronic controller 106 through the external interface 118. The driver 111 may provide an interface between the OS 109 and the electronic controller 106. Accordingly, the computing device 108 may comprise a programmable device that includes machine-readable instructions, for example, on non-transitory processor/computer readable-media (e.g., the memory).

The computing device 108 may further include a display 120 through which the OS 109 may provide a user interface (UI) 122. A user may use the UI 122 to interact with the OS 109 and the driver 111 to control the computing device 108, electronic controller 106, and/or the microfluidic chip 102. For example, the user may use the UI 122 to initiate a microfluidics application, and select a test to perform on a biologic sample, using the microfluidic chip 102. As used herein, a user may refer to a healthcare professional and/or a patient. However, examples are not so limited, and a user may refer to users other than healthcare professionals and patients.

The computing device 108 may also display data received from the electronic controller 106. For instance, the computing device 108 may display data collected, displayed, and/or analyzed by the microfluidic chip 102. In some examples, data displayed on the UI 122 of the computing device 108 may include a diagnosis, such as diagnosis of a blood clotting disorder. Additionally and/or alternatively, data displayed on the UI 122 of the computing device 108 may include a graph, table, and/or other summary describing data collected using the microfluidic chip 102. For example, the UI 122 of the computing device 108 may display data indicating a rate of coagulation of a blood sample. Examples are not so limited, however, and the UI 122 of the computing device 108 may display other forms of data collected with the microfluidic chip 102 relating to coagulation of a fluid sample. In some examples, the computing device 108 may be a portable computing device such as a "smart phone", a tablet computer, or other device.

The fluid reservoir 104 may be in fluidic communication with the microfluidic chip 102. In some examples, the fluid reservoir 104 is an external fluid reservoir, meaning that the fluid reservoir 104 is external to the microfluidic chip 102. For instance, the fluid reservoir 104 may be on cassette 101, where the cassette can receive the microfluidic chip 102. However, examples are not so limited, and the fluid reservoir 104 and/or a portion of the fluid reservoir 104 may be located on the microfluidic chip 102 itself (e.g., not on the cassette 101). For instance, a lower portion of the fluid reservoir 104 may be located on the microfluidic chip 102, while an upper portion of the fluid reservoir 104 may be located on the cassette 101. Collectively, the microfluidic chip 102 coupled to the cassette 101 may be referred to as a microfluidic device.

In some examples, the fluid reservoir 104 may hold and supply fluidic components/samples and/or solutions to the microfluidic chip 102. Various examples of the microfluidic chip 102 are described further herein and may generally include inlet/outlet chamber(s) 124, microfluidic channel(s) 126, actuator(s) 128, microfluidic filter(s) 130, sensor(s) 131, an electrical interface 132, and nozzle(s) 133. In some examples, the structures and components of the microfluidic chip 102 may be fabricated using conventional integrated circuit microfabrication techniques such as thin film deposition, electroforming, laser ablation, anisotropic etching, sputtering, dry and wet etching, photolithography, casting, molding, stamping, machining, spin coating, laminating, and so on. Furthermore, the microfluidic chip 102 may be composed of a number of materials. For instance, the microfluidic chip 102 may include a bulk silicon substrate which is microfabricated to form the microfluidic channels 126 and/or the sensor(s) 131. Additionally, the microfluidic chip 102 may include microfluidic channels 126 formed out of a photo imagable polymer, such as SU-8.

The electronic controller 106 may be coupled to the microfluidic chip 102 and may enable transmission of information and/or power between the computing device 108 and the microfluidic chip 102. In some examples, the electronic controller 106 may include a controller 134, I/O circuits 136, and a memory 138. Further, the electronic controller 106 may receive power from the computing device 108, such as through a USB cable. However, examples are not so limited, and the electronic controller may include a power supply 142.

The memory 138 may store hardware with instructions 140, which may include instructions executable by the controller 134 for controlling the microfluidic chip 102 and communicating with the computing device 108. For example, the hardware with instructions 140 may include instructions executable by the controller 134 for controlling the sensors 131 on the microfluidic chip 102. Accordingly, the electronic controller 106 may comprise a programmable device that includes machine-readable instructions stored in the form of software modules, for example, on non-transitory processor/computer readable-media (e.g., the memory). All or a portion of the electronic controller 106 may be implemented using a programmable logic device (PLD), application specific integrated circuit (ASIC), or the like. As used herein, a computing module can include computer executable instructions, hardware components (e.g., various forms of transistor logic, application specific integrated circuits (ASICs), etc.), or a combination thereof. But a computing module at least includes instructions executable by a processing resource, e.g., in the form of modules, to perform particular actions, tasks, and functions described in more detail herein.

In some examples, the sensor(s) 131 may be disposed in the channel(s) 126 near inlet(s) of the channel(s) 126 (e.g., closer to the fluid reservoir 104 than the actuator(s) 128). In another example, the sensor(s) 131 may be disposed in the inlet of the channel(s) 126. The sensor(s) 131 may be an impedance sensor formed using various semiconductor formation techniques. The sensor(s) 131 may detect impedance changes as particles in the fluid sample pass over and/or near the sensor(s) 131, as discussed further herein.

Further, the actuator(s) 128 may be disposed near a closed end of the channel(s) 126 downstream from the sensors 131. The actuator(s) 128 may be implemented using a wide variety of structures suitable to communicate a fluid sample through the channels 126. For example, the actuator(s) 128 may be a thermal resistor(s) that produces vapor bubbles to create fluid displacement of the fluid sample within the channel(s) 126. Actuators 128 may also be implemented as piezo elements (e.g., PZT) whose electrically induced deflections generate fluid displacements within the channel(s) 126. Other deflective membrane elements activated by electrical, magnetic, and other forces are also possible for use in implementing the actuator(s) 128.

The fluid sample (e.g., the fluid sample received by the fluid reservoir 104) may be ejected from nozzle(s) 133 on the microfluidic chip 102. A nozzle may refer to an ejection nozzle suitable for use with actuator(s) 128. Further, the nozzle(s) 133 may be disposed in or along the channel(s) 126, as discussed further herein. For example, nozzle(s) 133 may be adjacent to the sensor(s) 131 in the channel(s) 126.

While the above described elements and configurations are illustrated in FIG. 1 the present disclosure is not so limited. Rather, more or less components may be included in the microfluidic sensing system 100, in the microfluidic chip 102, an electronic controller 106, and a computing device 108 and/or arranged in various configurations, as described herein. Additionally while a particular number of elements are illustrated (e.g., a single channel 126) there may be more (e.g., two or more channels 126) and/or less of various elements such as the fluid reservoir 104, the channel(s) 126, the actuator(s) 128, filters(s) 130, the electrical interface 132, the sensor(s) 131, the nozzles 133, etc. depending upon a desired application of the microfluidic sensing system 100.

Figure 2:
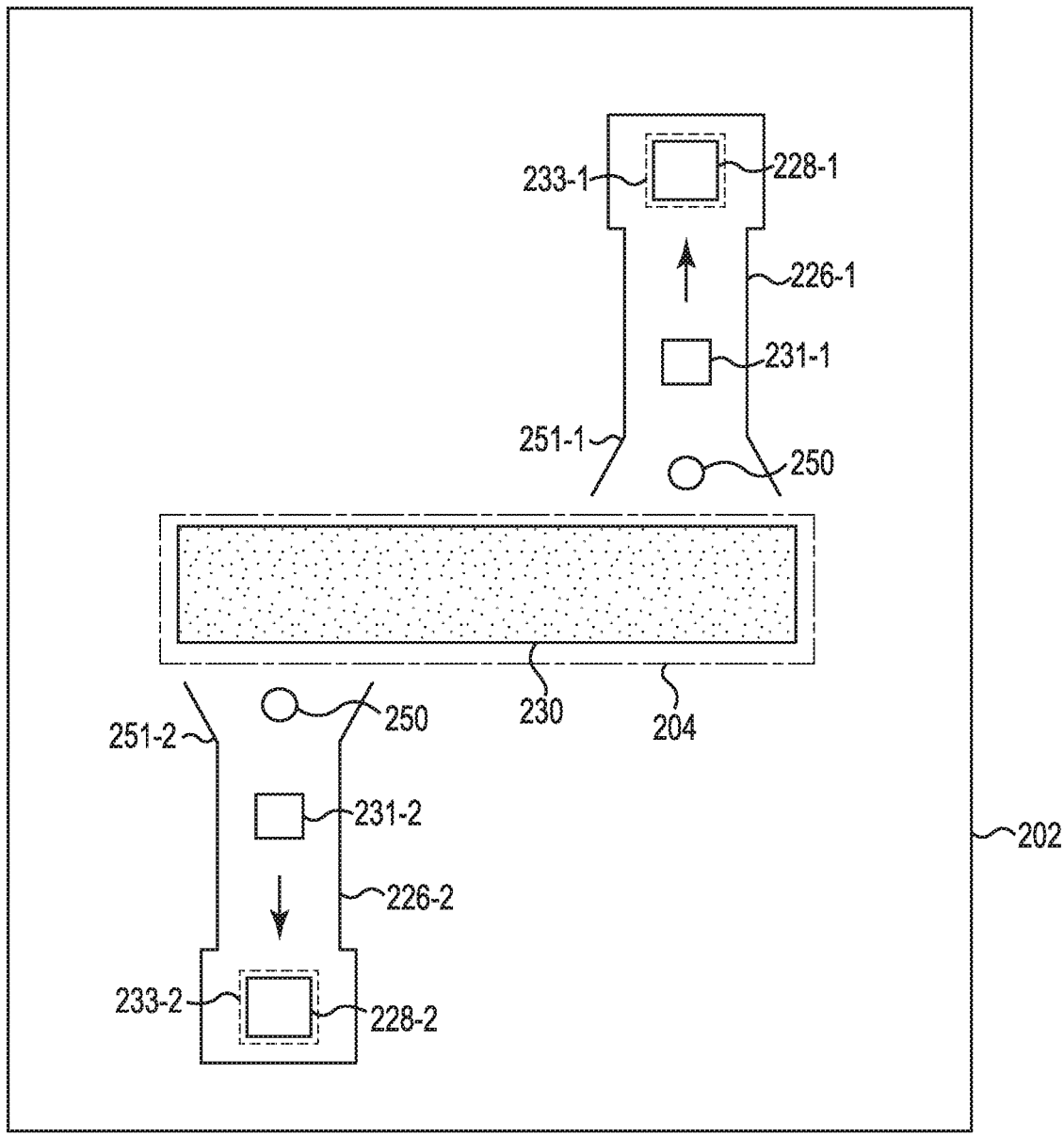
FIG. 2 illustrates a schematic diagram of an example of a microfluidic chip for coagulation sensing, according to the present disclosure.

FIG. 2 illustrates a schematic diagram of an example of a microfluidic chip 202 for coagulation sensing, according to the present disclosure. As illustrated in FIG. 2, the microfluidic chip 202 may include a plurality of channels 226-1, 226-2 (collectively referred to as channels 226), such as microfluidic channels, actuators 228-1, 228-2 (collectively referred to as actuators 228), sensors 231-1, 231-2 (collectively referred to as sensors 231), inlets 251-1, 251-2 (collectively referred to as inlets 251) to receive a fluid sample 250 from a fluid reservoir 204, and nozzles 233-1, 233-2 (collectively referred to as nozzles 233). As used herein, a nozzle refers to an outlet and/or opening from the channels 226. Additionally, as illustrated in FIG. 2, each nozzle 233 may be at an end of a microfluidic channel 226.

The inlet 251 may provide an opening for the channel 226 to receive the fluid sample. In some examples, a filter 230 may be disposed in the inlet 251. The filter 230 may prevent particles in the fluid sample of a particular size (depending on the size of the filter 230) from entering the channel 226. The inlet 251 may have a larger width and volume than the channel 226. That is, a volume of the inlet 251 may be greater than a volume of the channel 226. Inlet 251 may enable a fluid sample to flow from the fluid reservoir 204 into the channel 226.

The microfluidic channel 226 may also include narrowing portions. The narrowing portions may each be a portion of the respective microfluidic channel 226 having a narrower diameter than the inlet 251. The narrowing portion may be distal to the fluid reservoir 204, relative to the inlet 251. In some examples, the nozzle 233 (e.g., the outlet) may be included within the narrowing portion of the microfluidic channel 226. Examples are not so limited, however, and the microfluidic channel 226 need not narrow relative to the inlet 251. For instance, the microfluidic channel 226 may be the same width as the inlet 251. As described further herein, the nozzle 233 (e.g., outlet) may have an air interface, such that the nozzle 233 is exposed to air.

Further, the microfluidic chip 202 may include sensors 231, such as impedance sensors, located within each microfluidic channel 226. As used herein, an impedance sensor may determine a change in impedance, for instance, to determine a stage of a coagulation cascade of a blood sample (e.g., fluid sample 250) flowing through a microfluidic channel 226 to the impedance sensor (e.g., sensor 231). The sensors 231 may be within a particular proximity to the nozzle 233. For instance, the sensor 231 may be less than 100 micrometers (μm) from the nozzle 233. Examples are not so limited, however, and the sensor 231 may be directly beneath the nozzle 233. In other words, the sensor 231-2 may be located a distance away from the inlet 251-2 that is equal to the distance that the nozzle 233-2 is from the inlet 251-2.

As used herein, a coagulation cascade refers to a series of stages involved in the formation of a blood clot. Generally, the coagulation cascade may include: a first stage including activation, adhesion, and aggregation of platelets to form a soft plug; a second stage including formation and propagation of fibrin strands; and a third stage including formation of a full hemostatic plug.

As used herein, the first stage of the coagulation cascade may be referred to as primary hemostasis. When blood cells are exposed to air, such as by exposure through the outlet 228 in the microfluidic chip 202, platelet adhesion may begin. Platelet adhesion includes the release of various granules, such as serotonin, platelet-activating factor (PAF), platelet factor 4, and thromboxane A2, among others. The release of these granules may cause a change in the shape of the platelets in the blood sample, and subsequent adhesion of the platelets. Adhesion of the platelets may subsequently lead to the formation of a "soft plug", which signifies the end of the first stage of the coagulation cascade.

The second stage of the coagulation cascade may be referred to as secondary hemostasis, and may result in stabilizing the soft plug formed during primary hemostasis. The second stage of the coagulation cascade may include formation and propagation of fibrin strands. Fibrin strands refer to fibrous, non-globular proteins involved in the clotting of blood. The formation of fibrin strands includes polymerization of fibrinogen with a protease thrombin. The formed fibrin strands further propagate, or multiply, and the polymerized fibrin strands, together with platelets, may form a full hemostatic plug, also referred to as a clot. As used herein, the formation of a full hemostatic plug refers to the third stage of the coagulation cascade.

As described further herein, the sensor 231 may detect a change in impedance in response to detecting which stage of the coagulation cascade a blood sample (e.g., fluid sample 250) is in. For instance, an impedance sensor (e.g., sensor 231) may detect a change in impedance in response to detection of aggregated platelets in the blood sample. In another example, the impedance sensor may detect a change in impedance in response to detection of a soft plug in the blood sample. Further, the impedance sensor may detect a change in impedance in response to detection of formed fibrin strands and/or detection of fibrinogen in the blood sample. Additionally, the impedance sensor may detect a change in impedance in response to detection of a full hemostatic plug in the blood sample.

The microfluidic chip 202 may also include an actuator 228 disposed near an end of the channel 226 downstream from the sensor 231. The actuator 228 may be a fluidic inertial actuator, which may be implemented using a wide variety of structures. For example, the actuator 228 may be a pump, such as a thermal resistor pump that produces vapor bubbles to create fluid displacement within the channel 226. The resistor pump (e.g., actuator 228) may accelerate the flow of the fluid sample 250, such as a flow of blood cells, through the microfluidic channel 226. The displaced fluid sample 250 may be ejected from the nozzle(s) 223.

In some examples, the sensor 231 may be disposed in the channel 226. The sensor 231 may be an impedance sensor formed using various semiconductor techniques. The sensor 231 may detect impedance changes as particles in the fluid sample pass over the sensor 231.

As illustrated in FIG. 2, the microfluidic chip 202 may include a plurality of channels 226, a plurality of inlets 251, a plurality of sensors 231, etc. As such, the microfluidic chip 202 may include a plurality of microfluidic channels to direct the flow of a blood sample, such as fluid sample 250. Fluid sample 250 may be directed down each of the plurality of channels 226. While FIG. 2 illustrates two inlets 251, two sensors 231, two channels 226, etc., examples are not so limited. The microfluidic chip 202 may include more or less features than illustrated in FIG. 2.

Each of the plurality of channels 226 (e.g., microfluidic channels) may have an outlet at the end. The fluid sample 250 may flow away from the fluid reservoir 204 and toward an end of each of the plurality of channels 226. For instance, fluid sample 250 may flow into inlet 251-1, into the channel 226-1 and over the sensor 231-1, and toward the nozzle 233-1 at the end of the channel 226-1. As described herein, each of the nozzles 233 may be an outlet in the channel, and therefore have an air interface. In some examples, each of the nozzles 233 may range in diameter from 5-100 micrometers ($\mu m$). Furthermore, the placement of the nozzles 233 in the channels 226, combined with the air interface of the nozzles, may simulate the flow of blood to a wound and may allow for detection of the different stages of the coagulation cascade without using any reagent and/or activating agent.

In an example, a filter 230 (e.g., a mesh filter) may be provided in the fluid reservoir 204 for filtering particles in the applied fluid sample. While the shape of the fluid channels 226 is shown as being straight, this is not intended as a limitation on the shape of the channels 226. Thus, the shape of the channels 226 may include other shapes, such as curved shapes, snake-like shapes, shapes with corners, combinations thereof, and so on. Moreover, the channels 226 are not shown to any particular scale or proportion. The width of the channels 226 as fabricated on a device may vary from any scale or proportion shown in the drawings of this disclosure. In some examples, the width of the channels 226 may range from 500 nm-500 $\mu m$, resulting in a highly sensitive system for detecting the various stages of the coagulation cascade.

Additionally, microfabricated resistive elements inside or in close promixity to the microfluidic channel 226 (not illustrated in FIG. 2) may provide controlled heating of the fluid sample to expedite and/or accelerate the flow, migration, evaporation, and/or coagulation of the fluid sample. The resistive elements may be driven by application of a voltage, for instance, between 1 and 30 volts (V) for a particular duration of time, such as 1 to 20 microseconds ($\mu s$). The temperature feedback may be provided by means of a Thermal Sense Resistor.

Figure 3:
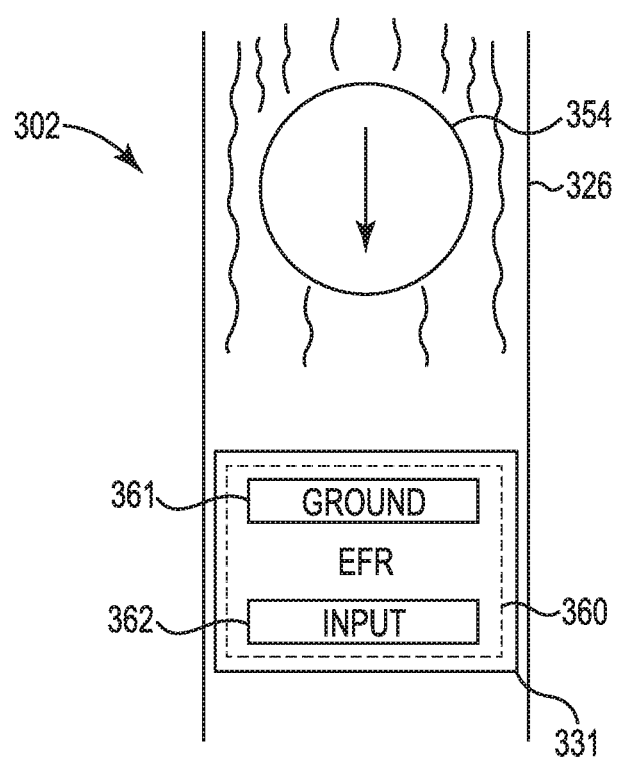
FIG. 3 further illustrates an example of a microfluidic chip, according to the present disclosure.

FIG. 3 further illustrates an example of a microfluidic chip 302 according to the present disclosure. Particularly, FIG. 3 illustrates a close up view of a sensor 331 and related structures in the microfluidic chip 302.

Microfluidic chip 302 may include a channel 326 and a sensor 331, such as an impedance sensor. As described herein, channel 326 may comprise a microfluidic passage through which fluid including particles 354 may pass through. For purposes of this disclosure, the term "particle" encompasses any small minute piece, fragment or amount, including, not limited to, a biological cell or group of biological cells, components of blood such as platelets, components of a blood clot such as fibrin and/or fibrinogen, and/or a hemostatic plug, among others. Channel 326 may direct the flow of fluid and particles 354 across and/or through an electric field region (EFR) 360 (schematically illustrated) formed within channel 326 by sensor 331.

The sensor 331 may form the EFR 360 within channel 326. The sensor 331 may include an electrical ground 361 and an input electrode 362 which cooperate to form a region 360 of electric field lines that extend within an area of channel 326. As used herein, an electrical ground 361 may include an input low-side electrode, and an input electrode 362 may include an input high-side electrode. Electric ground 361 and input electrode 362 may both be "local" in that electric ground 361 and input electrode 362 are provided by electrically conductive contacts adjacent to the interior of channel 326 or in relatively close proximity to the interior of channel 326, such as just below or behind an interior surface or skin of channel 326. In contrast to a remote ground located outside of channel 326 or distant channel 326, a substantial majority, if not all, of the electric field region 360 between ground 361 and input electrode 362 is contained within the interior of channel 326. As a result, the distance that the electric field lines between ground 361 and input electrode 362 extend is not so long as to reduce or weaken signal strength to a point that substantially impairs accuracy of impedance detection. While the above example describes a ground and electrode, embodiments are not so limited. In some embodiments, an input high-side electrode and an input low-side electrode may be used to form a region (e.g., such as region 360) of electric field lines.

As illustrated in FIG. 3, the input electrode 362 may be located close to the reservoir where blood may collect. For instance, input electrode 362 may be located proximal to the nozzle (233-1 and/or nozzle 233-2, illustrated in FIG. 2), relative to the electric ground 361. Similarly, the electric ground 361 may be located distal to the nozzle (233-1 and/or nozzle 233-2, illustrated in FIG. 2), relative to the input electrode 362. Put another way, the sensor (e.g., impedance sensor) may be located adjacent to the nozzle, and may determine a stage of coagulation in the blood sample due, in part, to the proximity of the sensor to the nozzle.

In some examples, the thickness of the electric ground 361 and input electrode 362 may range from 100 Angstroms (A) to 5000 A. Additionally, the distance between the electric ground 361 and the input electrode 362 may range from 2 $\mu m$ to 50 $\mu m$. Examples are not so limited, however, and the electrodes may have other thicknesses and may be spaced at greater or lesser distance than that described herein.

When fluid passes through EFR 360, the electric field lines of region 360 may be at least partially obstructed by the fluid such that the electric field lines of region 360 may be altered and travel around particles in the fluid. The increased length of the electric field lines of EFR 360, resulting from having to travel around particles in the fluid, may change (e.g., increase) the electrical impedance that may be detected at input electrode 362. As a result, the increase in impedance resulting from obstruction of EFR 360 by the fluid may serve as an indicator of a stage of coagulation of the blood (e.g., the fluid) in the channel.

In some examples, the input electrode 362 and ground 361 may be positioned such that a stage of coagulation may be detected as soon as blood starts to coagulate. For example, nozzles (e.g., nozzles 233 illustrated in FIG. 2) may be located in close proximity to the input electrode 362 and ground 361. When blood (e.g., the fluid) flows through the channels (e.g., channels 226 illustrated in FIG. 2), the air interface in the nozzles may cause the coagulation cascade to begin. As the blood coagulates and flows over the input electrode 362, the electric field between the ground 361 and input electrode 362 may change. For example, adhered platelets may deflect the EFR 360 and cause a change in impedance within a threshold range associated with adhered platelets. Similarly, fibrin strands may deflect the EFR 360 and cause a change in impedance within a threshold range associated with fibrin strands. Furthermore, a full hemostatic plug may deflect the EFR 360 and cause a change in impedance within a threshold range associated with a full hemostatic plug.

Figure 4:
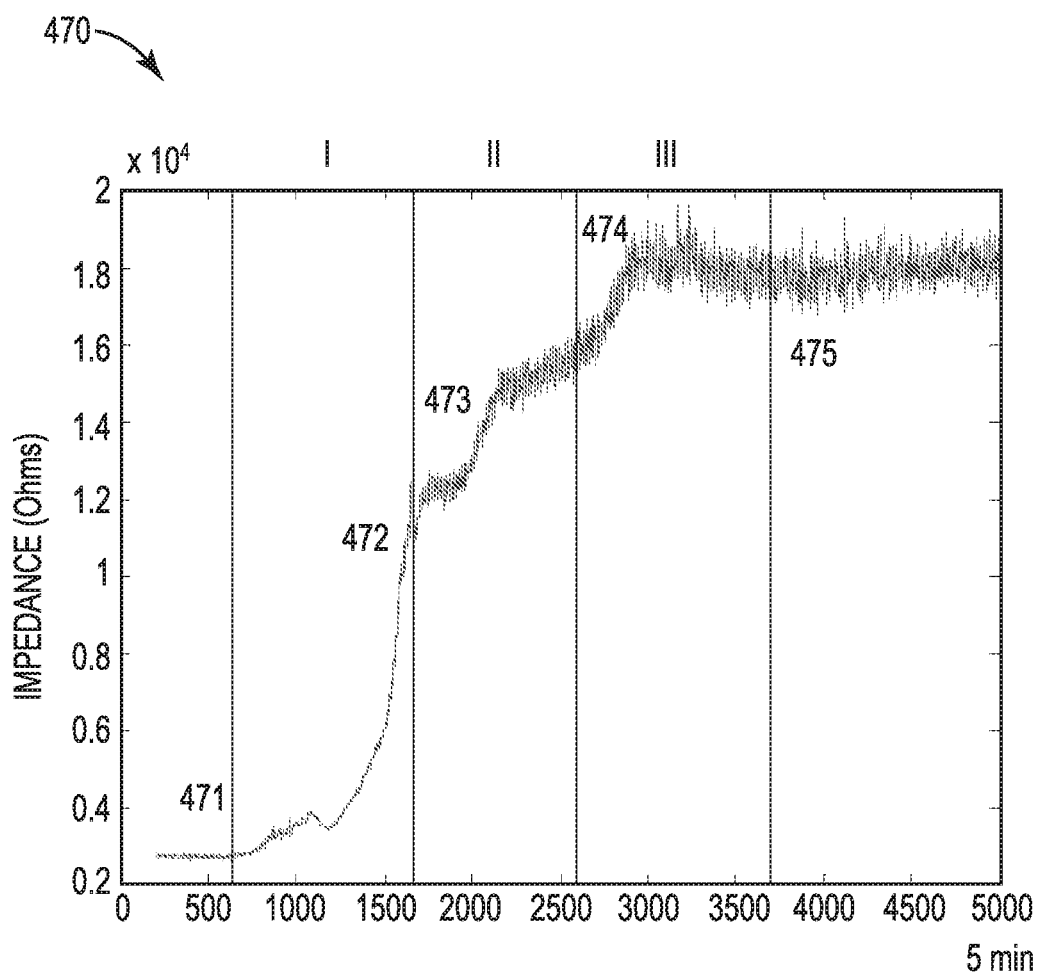
FIG. 4 illustrates a graphical representation of impedance changes during a coagulation cascade, as detected with a microfluidic chip, according to the present disclosure.

FIG. 4 illustrates a graphical representation 470 of impedance changes during a coagulation cascade, as detected with a microfluidic chip, according to the present disclosure. As described in relation to FIG. 3, as blood coagulates within channels in the microfluidic chip and flows over the electrode, the electric field between the ground and electrode may change. The change in this electric field may cause a change in impedance, which may be monitored over a period of time. In some examples, the stage of coagulation (e.g., the stage of the coagulation cascade) may be determined based on a change in impedance detected by the sensor. For instance, in response to the impedance changing from a first value to a second value different than the first value (e.g., greater) during a threshold period of time, such as 2 minutes, a particular stage of coagulation may be detected.

For instance, at 471, a blood sample (e.g., fluid 250 illustrated in FIG. 2) may migrate toward the nozzles (e.g., nozzles 233 illustrated in FIG. 2) within the microfluidic chip (e.g., microfluidic chip 202 illustrated in FIG. 2). As blood migrates toward the nozzles, impedance may remain at a level that is not associated with components of the coagulation cascade, such as less than $0.4 \times 10^4$ Ohms ($\Omega$). In other words, the sensor may detect a lack of coagulation components, such as adhered platelets, aggregated platelets, fibrin strands, and/or a hemostatic plug, in response to detecting an impedance level of less than $0.4 \times 10^4 \Omega$.

At 472, the first stage (indicated by the Roman numeral "I" on the top of graphical representation 470) of the coagulation cascade may be detected. For example, platelets adhering near the nozzles (e.g., nozzles 233 illustrated in FIG. 2) may result in an impedance level associated with platelet adhesion, such as between $0.4 \times 10^4 \Omega$ and $1.0 \times 10^4 \Omega$. At 473, the first stage of the coagulation cascade may further be determined by detecting the aggregation of platelets near the nozzles. For instance, platelets aggregating near the nozzles may result in an impedance level associated with aggregated platelets, such as between $1.0 \times 10^4 \Omega$ and $1.6 \times 10^4 \Omega$.

At 474, the second stage (indicated by the Roman numeral "II" on the top of graphical representation 470) of the coagulation cascade may be detected. For example, the formation and propagation of fibrin strands near the nozzles may result in an impedance level associated with formed fibrin strands, such as between $1.6 \times 10^4 \Omega$ and $1.8 \times 10^4 \Omega$.

Additionally, at 475, the third stage (indicated by the Roman numeral "III" on the top of graphical representation 470) of the coagulation cascade may be detected. For example, the formation of a full hemostatic plug near the nozzles may result in an impedance level associated with a formed hemostatic plug, such as $1.8 \times 10^4 \Omega$ and higher. While impedance levels have been provided herein for illustration, examples of the present disclosure are not so limited. Impedance values for each stage of the coagulation cascade may be greater or lesser than the values described herein.

In the present disclosure, reference is made to the accompanying drawings that form a part hereof, and in which is shown by way of illustration how a number of examples of the disclosure may be capable of being practiced. These examples are described in sufficient detail to enable those of ordinary skill in the art to practice the examples of this disclosure, and it is to be understood that other examples may be capable of being used and that process, electrical, and/or structural changes may be capable of being made without departing from the scope of the present disclosure.

The figures herein follow a numbering convention in which the first digit corresponds to the drawing figure number and the remaining digits identify an element or component in the drawing. Elements shown in the various figures herein may be capable of being added, exchanged, and/or eliminated so as to provide a number of additional examples of the present disclosure. In addition, the proportion and the relative scale of the elements provided in the figures are intended to illustrate the examples of the present disclosure, and should not be taken in a limiting sense.

Further, as used herein, "a" or "a number of" something may refer to one or more such things. For example, "a number of widgets" may refer to one or more widgets. Also, as used herein, "a plurality of" something may refer to more than one of such things.

The above specification, examples and data provide a description of the method and applications, and use of the system and method of the present disclosure. Since many examples may be capable of being made without departing from the spirit and scope of the system and method of the present disclosure, this specification merely sets forth some of the many possible example configurations and implementations.

What is claimed is:

1. A microfluidic chip, comprising:
 a microfluidic chip;
 an outlet at an end of the microfluidic channel having an air interface; and
 an impedance sensor located within the microfluidic channel at the outlet having the air interface, the impedance sensor configured to determine a stage of a coagulation cascade of a blood sample flowing through the microfluidic channel to the impedance sensor.

2. The microfluidic chip of claim 1, further comprising a resistor pump in the microfluidic channel to accelerate a flow of the blood sample through the microfluidic channel and eject the blood sample from a nozzle at the end of the microfluidic channel.

3. The microfluidic chip of claim 1, further comprising a plurality of microfluidic channels, each channel ending in a nozzle with an air interface and an impedance sensor to detect a change in impedance in response to detection of aggregated platelets in the blood sample, the nozzles arranged to simulate flow of blood to a wound without introduction of any reagent to the blood sample.

4. The microfluidic chip of claim 1, further comprising a resistive element inside the microfluidic channel to provide controlled heating of the blood sample to with a temperature feedback provided by a Thermal Sense Resistor.

5. The microfluidic chip of claim 1, further comprising a filter located at an inlet of the microfluidic channel, the microfluidic channel having a narrowing portion by which the microfluidic channel narrows to a smaller diameter in a direction away from the inlet.

6. The microfluidic chip of claim 1, further comprising the impedance sensor to detect a change in impedance in response to detection of a full hemostatic plug in the blood sample.

7. The microfluidic chip of claim 1, further comprising:
 a plurality of microfluidic channels to direct a flow of a blood sample, wherein each of the plurality of microfluidic channels includes a nozzle at the outlet having an air interface, the nozzle being a fluid outlet for fluid to exit the microfluidic channel;
 each of the microfluidic channels having a respective impedance sensor, each impedance sensor including an input high-side electrode and an input low-side electrode, the input high-side electrode proximal to the air interface relative to the input low-side electrode, each impedance sensor to detect a stage of coagulation of the blood sample during a period of time, based on a change of impedance detected by each impedance sensor; and an electrical output to output an electrical signal representing sensed data from the multiple impedance sensors.

8. The microfluidic chip of claim 7, wherein the nozzle has a diameter of less than 100 micrometers.

9. The microfluidic chip of claim 7, wherein the input high-side electrode and the input low-side electrode are separated by a distance of less than 50 micrometers.

10. The microfluidic chip of claim 8, wherein each of the input high-side electrode and the input low-side electrode have a thickness of less than 5000 Angstroms.

11. The microfluidic chip of claim 1, further comprising:
an input for connection to a cassette that includes a fluid reservoir, the input to receive a blood sample from the cassette;
the microfluidic channel to direct a flow of the blood sample to a nozzle at the outlet at an end of the microfluidic channel, the nozzle having the air interface to accumulate the blood sample; and
the sensor having an input electrode proximal to the nozzle and an electric ground located distal to the nozzle.

12. The microfluidic chip of claim 1, further comprising a nozzle, wherein the nozzle is located within a narrowing portion of the microfluidic channel.

13. The microfluidic chip of claim 11, further comprising the impedance sensor to detect a primary hemostasis stage of coagulation in the blood sample in response to detecting an impedance value between $0.4 \times 10^4$ Ohms and $1.0 \times 10^4$ Ohms.

14. The microfluidic chip of claim 11, further comprising the impedance sensor to detect a secondary hemostasis stage of coagulation in the blood sample in response to detecting an impedance value between $1.6 \times 10^4$ Ohms and $1.8 \times 10^4$ Ohms.

15. The microfluidic chip of claim 11, further comprising the impedance sensor to detect a full hemostatic plug in response to detecting an impedance value of at least $1.8 \times 10^4$ Ohms.

16. A microfluidic chip, comprising:
a microfluidic channel;
an outlet at an end of the microfluidic channel having an air interface; and
an impedance sensor located within the microfluidic channel, the impedance sensor to determine a stage of a coagulation cascade of a blood sample flowing through the microfluidic channel to the impedance sensor;
wherein the sensor is located less than 100 micrometers (μm) from the outlet having the air interface.

17. The microfluidic chip of claim 16, wherein the sensor and the outlet are located a same distance away from an inlet of the microfluidic channel.

* * * * *